United States Patent [19]

Guigues

[11] Patent Number: 4,579,457

[45] Date of Patent: Apr. 1, 1986

[54] APPARATUS FOR MEASURING OPTICALLY AND CONTINUOUSLY THE HYDROCARBON CONTENT IN A LIQUID

[76] Inventor: Frédéric Guigues, "Le Capri" - Bâtiment A - rue de Cuques, 13100 - AIX-en-Provence, France

[21] Appl. No.: 589,578

[22] Filed: Mar. 14, 1984

[30] Foreign Application Priority Data

Mar. 31, 1983 [FR] France .................. 83 05489

[51] Int. Cl.⁴ .................................. G01N 21/00
[52] U.S. Cl. .................................. 356/436
[58] Field of Search .......................... 356/436

*Primary Examiner*—Bernard D. Pianalto
*Attorney, Agent, or Firm*—Balogh, Osann, Kramer, Dvorak, Genova & Traub

[57] ABSTRACT

The invention relates to a process and apparatus for measuring, optically and continuously, the hydrocarbon content in a liquid. An apparatus according to the invention is placed on board an oil tanker comprising a partition which separates a front compartment of inherent safety from a rear compartment. A continuous sample of deballast water from the tanks is taken via a conduit. This sample is clarified in a centrifuge, driven by a motor, which eliminates the particles in suspension. The liquid leaving the centrifuge is emulsified then it passes into an optical measuring cell comprising two optical fibers which connect the cell to an electronic cabinet placed in the rear compartment. One application of the invention is the monitoring of the hydrocarbon content of the deballast water in oil tankers.

4 Claims, 4 Drawing Figures

APPARATUS FOR MEASURING OPTICALLY AND CONTINUOUSLY THE HYDROCARBON CONTENT IN A LIQUID

The present invention relates to a process and apparatus for optically measuring, in a very short time, the content, which may even be very low, of hydrocarbons in a liquid, particularly the deballast water rejected by oil tankers, containing particles in suspension.

The technical sector of the invention is that of the construction of optical measuring apparatus.

It will be recalled that, when they unload their cargo of hydrocarbons, oil tankers must put water in their tanks to act as ballast. This water is pumped in the port of delivery. The majority of large oil ports lie near an estuary and the water in the port is frequently laden with particles of silt brought down by the river and is therefore more or less turbid.

During their return trip to a loading station, oil tankers proceed with emptying the ballast into the open sea in order to wash the tanks and replace the first ballast water by cleaner water which may be rejected directly into the sea near the port of loading. There are regulations concerning rejection of the deballast water into the sea in order to avoid too great a pollution of the seas. International regulations prohibit rejecting into the sea water containing more than 60 liters of hydrocarbons per nautical mile, which corresponds to 100 mg/liter for a ship advancing at 15 knots and rejecting 9000 m$^3$/hour. Oil tankers comprise a special decantation tank, called "slop-tank", in which it is possible to decant the water in order to separate it from the sediments in suspension and from part of the hydrocarbons so as to reject into the sea water which complies with the standard regulations.

Monitoring of the hydrocarbon content of the deballast water of oil tankers requires reliable measuring apparatus capable of detecting in a relatively short time hydrocarbon contents which may be very low. These measuring apparatus are generally associated with automatic controls which stop pumping of the water or discharge into the sea if the hydrocarbon content measured exceeds a determined threshold. They are also associated with a recorder, of the black box type, which memorizes the hydrocarbon contents measured during deballasting operations and which makes it possible to monitor a ship upon arrival in a port and to penalize it if the authorized theshold has been exceeded.

The measuring apparatus intended for monitoring the hydrocarbon content of deballast water must be approved by the Intergovernmental Maritime Consultative Organisation, abbreviated to I.M.C.O.

The hydrocarbon content of deballast water may be monitored by apparatus employing different methods. These include optical apparatus which monitor the hydrocarbon content by measuring the turbidity or opacity of the mixture of water and hydrocarbons after having finely emulsified the droplets of hydrocarbons.

French Pat. No. 71 33128 and Certificate of Addition No. 72 42946 to Jacques PERIERES describe optical turbidity detectors comprising an optical measuring cell or optical sensor, composed of a light source, a photoelectric receiver and optical fibers which are located inside two transparent tubes, which are disposed in alignment on either side of a conduit in which the liquid to be monitored circulates. An emulsifier is advantageously placed upstream of the optical measuring cell.

The optical apparatus described in these two prior Patents were approved by the I.M.C.O. to equip monitoring and recording stations to board the oil tankers. They present three interesting advantages. The response time of these apparatus is less than 10 seconds, therefore clearly less than the threshold of 20 seconds imposed by the I.M.C.O. regulations, and this thanks to the high speed of passage of the water in the measuring cell which enables very short response and measuring times to be obtained.

Those parts of the optical measuring cell which are in contact with the hydrocarbon-laden water, i.e. the ends of the transparent tubes which contain the optical fibers, are automatically cleaned by the high-speed passage of the water which avoids hydrocarbons being deposited on the transparent walls and therefore avoids errors in measurement by excess of the hydrocarbon content.

Finally, these optical apparatus comply with the intrinsic safety regulations against the risks of fire or explosion of the installations processing the hydrocarbons.

In fact, the electrical parts of the measuring cell which are constituted by the light emitter and by the photoelectric receiver are located in the rear compartment of the oil tanker where the presence of electrical installations is allowed. This compartment is separated from the front compartment by a partition, which is traversed by the optical fibers which extend the light emitter on the one hand and the photoelectric receiver on the other hand, so that none of the parts of the optical measuring cell located in the front compartment, where the hydrocarbon-laden water circulates, is made alive.

It has been seen that the ballast water which is pumped in the ports may contain silt or sediment in suspension which render the water more or less turbid. Moreover, sea water attacks the sheet steel constituting the tanks of the oil tanker, which leads to the presence, in the deballast water, of iron in colloidal form which reduces the transparency of the water.

The turbidity of the water due to the sediment, silt or colloidal iron is translated by an absorption of light during passage of the liquid through the optical measuring cell and this absorption is added in the absorption due to the hydrocarbons contained in the water. The hydrocarbon content measured by the apparatus is therefore falsified by excess by the presence of the impurities other than the hydrocarbons which are suspended in the water. This error is generally small and less than the standards imposed by the I.M.C.O. whereby the presence of 100 mg/liter of well-determined dust in suspension in water containing 500 mg/liter of light crude oil, must not increase the measurement of turbidity by more than 20%.

However, the measuring apparatus is most often associated with a recorder which records and calculates the total quantity of hydrocarbons rejected into the sea and in particular the quantity exceeding an approved threshold, and the ship owner is penalized in proportion to the quantity calculated.

In that case, the theoretical quantity of hydrocarbons calculated is falsified by excess if the water is rendered opaque by rust or sediment or silt in suspension and the ship owner is unjustly penalized by discharging into the sea impurities other than hydrocarbons which are not subjected to any regulations.

This cause of error is a hindrance to the use on oil tankers of apparatus for optically monitoring deballast water.

To solve this difficulty, French Patent Application No. 79 03915 (to S.E.R.E.S.) has proposed a process whereby the hydrocarbons are extracted by means of a solvent, the opacity of the liquid before extraction of the hydrocarbons and that of the remaining liquid after extraction of the hydrocarbons are measured separately and the two opacities measured are compared.

The apparatus carrying out this latter process makes it possible to eliminate the error of measurement on the hydrocarbon content due to the presence of opaque impurities other than hydrocarbons, but it takes at least 10 minutes to extract the hydrocarbons by solvent, this leading to too long a response time which is incompatible with the response time of less than 20 seconds imposed by the I.M.C.O.

It is an object of the invention to provide a novel process which makes it possible to construct optical apparatus for continuously measuring the hydrocarbon content of deballast water, which eliminate the errors in measurement due to the presence of opaque impurities, in suspension in the water, other than the hydrocarbons.

This purpose is attained by a process for optically and continuously measuring the hydrocarbon content of a liquid, particularly deballast water in oil tankers, containing particles in suspension, the process including the following steps of:

continuously sampling a quantity of the liquid to be monitored, clarifying this liquid by eliminating by centrifugation the particles in suspension in the liquid, forming a very fine emulsion of the water and of the hydrocarbons emerging from the centrifuge, and continuously passing the emulsion in an optical measuring cell between a light emitter and a photoelectric receiver.

An optical apparatus according to the invention for continuously measuring the hydrocarbon content in a liquid, particularly deballast water in an oil tanker, containing particles in suspension, is of the known type including an optical measuring cell equipped with a light source and a light receiver between which said liquid circulates.

The aims of the invention are attained by means of an apparatus of this type which includes, upstream of said measuring cell, a centrifuge which clarifies the liquid by separating the particles in suspension and an emulsifier which mixes the hydrocarbons and the water emerging from the centrifuge, forming a very fine emulsion.

The invention results in the continuous optical measurement of the hydrocarbon content of a liquid, particularly deballast water in an oil tanker, by eliminating the errors of measurement by excess due to the particles in suspension in the liquid and, in particular, to the presence of silt, sediments or rust in the colloidal state in the deballast water in oil tankers.

Thanks to the centrifugation which precedes passage through the optical measuring cell, a thorough elimination of the particles in suspension is obtained and this elimination is effected continuously and very rapidly, in some seconds, so that there is no risk of recording erroneous measurements over a long period of time which risk penalizing the ship owner. Nor is there any risk of automatically stopping, in untimely manner, discharge into the sea of ballast water in the event of the hydrocarbon content therein being within the authorized limits and of the water containing opaque sediments or impurities other than hydrocarbons which are allowed to be discharged but which would risk being confused, by the apparatus, with hydrocarbons.

The addition of a centrifuge to an optical turbidity measuring apparatus makes it possible to obtain an apparatus having a response time of the order of 10 seconds, thus complying, from this standpoint, with the requirements for approval.

The addition at the outlet of the centrifuge of fixed deflectors which intimately mix the water and the hydrocarbons into a very fine emulsion makes it possible to replace the emulsifier vane pump, placed upstream of the optical measuring cell on the existing apparatus.

BRIEF DESCRIPTION OF THE DRAWINGS

The invention will be more readily understood on reading the following description with reference to the accompanying drawings, in which.

DETAILED DESCRIPTION OF THE DRAWINGS

Figure 1:
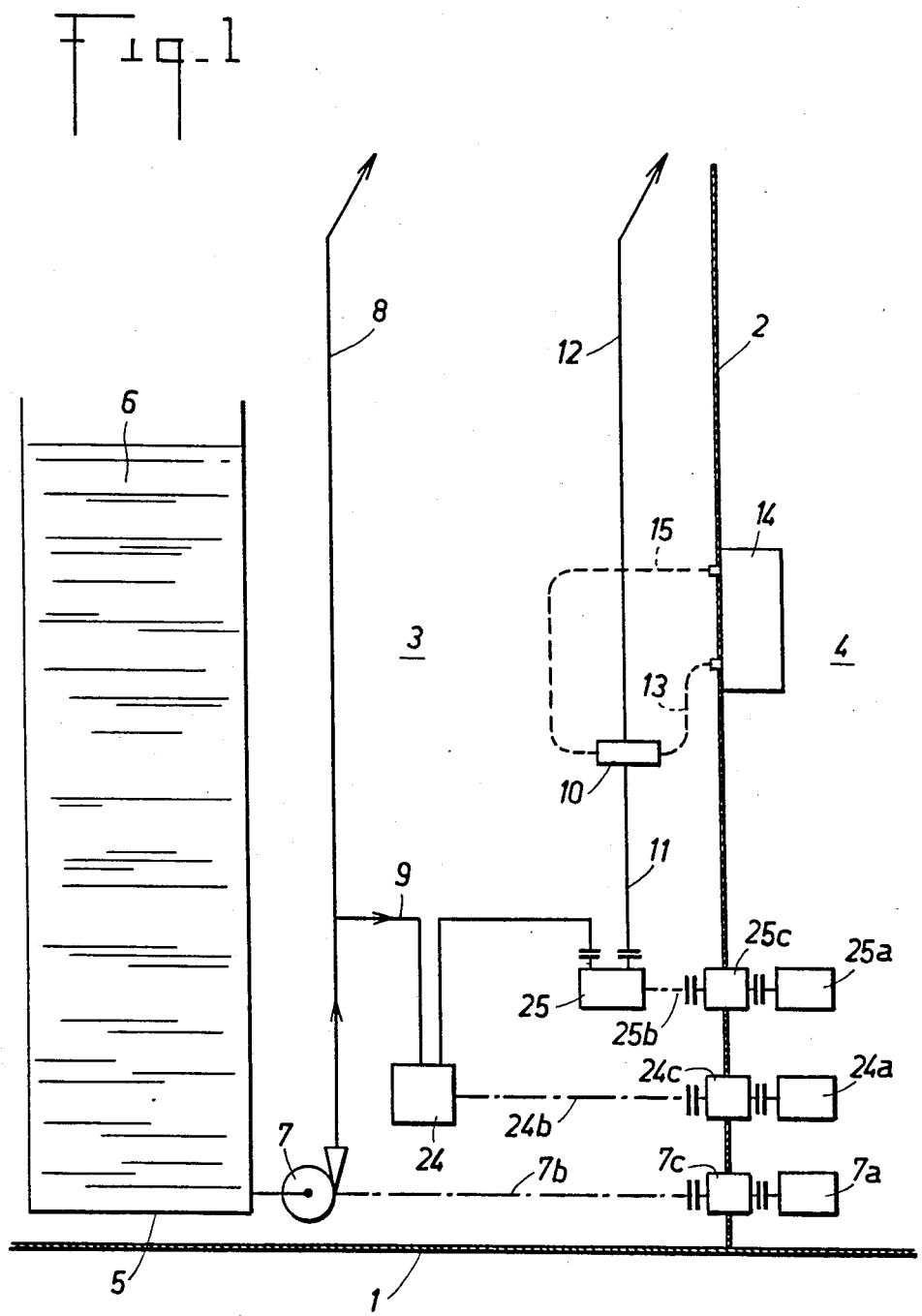
FIG. 1 is a schematic view of the whole apparatus according to the invention.

Referring now to the drawings, FIG. 1 schematically shows an overall view in elevation of an apparatus according to the invention installed on board an oil tanker. Reference 1 designates the bottom of the ship. Reference 2 represents a transverse partition which separates the ship into two compartments, a front compartment 3 where hydrocarbons are kept and a rear compartment 4 where the propelling machinery, the motors and all the electrical circuits are located. The front compartment 3 must comply with the standards of inherent safety intended to avoid any risk of inflammation or explosion of the hydrocarbons and in particular, it is prohibited to place in the front compartment electrical circuits or parts of machines which are live.

Reference 5 represents one of the tanks of the ship which contains hydrocarbons on the outward journey and which, on the return trip to a loading station, contains ballast water 6 which was pumped in the port of delivery and which is in contact with the hydrocarbons having adhered to the walls and with the sediments and silt containing heavy hydrocarbons which are deposited at the bottom of the tank.

FIG. 1 shows an optical apparatus for continuously monitoring the hydrocarbon content in the water during deballasting.

The water is pumped in the tanks by a deballasting pump 7 which is disposed in the front compartment 3. On the contrary, the motor 7a for driving the pump is installed in the rear compartment 4.

The shaft 7b connecting the motor to the pump is shown in chain-dotted lines. It passes through the partition 2 and a stuffing box 7c ensures tightness of the passage of the shaft through the partition 2.

Reference 8 represents the delivery pipe of pump 7 which rejects the water into the sea if the hydrocarbon content is less than the authorized threshold which is 60 liters/mile. If the hydrocarbon content is higher, an automatic system stops the pump.

To monitor the hydrocarbon content in the deballast water, a pipe 9 is connected to the delivery pipe 8. This pipe 9 diverts a small quantity of water towards an optical measuring cell 10.

The liquid to be monitored enters the cell 10 via a pipe 11, it passes through cell 10 continuously and emerges therefrom via a pipe 12 which directs the liquid towards the decanter installed in the ship.

The cell 10 comprises a light emitter which is placed in alignment with a light receiver.

The liquid to be monitored circulates between the emitter and the receiver and the liquid absorbs light more or less as a function of the relative opacity thereof.

By measuring the quantity of light reaching the receiver, the hydrocarbon content may be determined in the event of the liquid being a mixture of water and hydrocarbons.

The light emitter is constituted by one end of an optical fiber 13 which is engaged in a transparent tube of which the outer wall is swept by the liquid to be monitored.

The optical fiber 13 passes hermetically through the partition 2 and the other end of the fiber terminates in a cabinet 14 located in the rear compartment 4, in which is located a light source. It is specified that the term "light source" designates any source of electromagnetic radiations which may be visible, white or monochromatic light, light non-visible in the infrared or the ultraviolet or coherent radiations emitted by a laser source.

Similarly, the light receiver located in cell 10 is constituted by the end of an optical fiber 15 which is disposed inside a transparent tube. The fiber 15 passes hermetically through the partition 2 and terminates in the cabinet 14, opposite a photoelectric receiver which receives the light transmitted by fiber 15 and which converts it into an electrical signal which is converted by electronic circuits into a signal which measures the opacity of the sheet of liquid located between the ends of the two transparent tubes.

Figure 4:
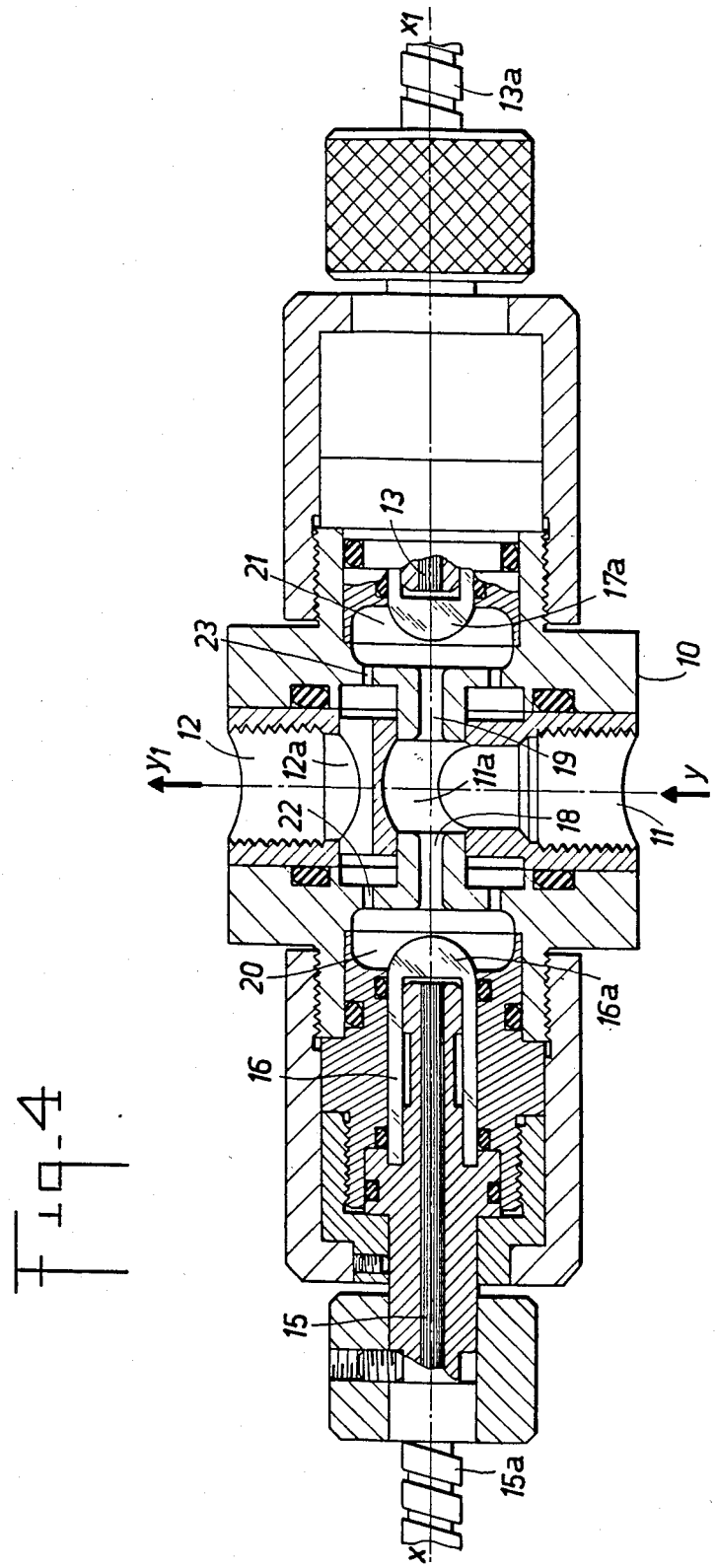
FIG. 4 is an axial section through an optical measuring cell equipping an apparatus according to the invention.

FIG. 4 is an axial section through a preferred embodiment of an optical measuring cell 10.

This Figure shows the pipe 11 through which the liquid to be monitored arrives and the pipe 12 through which it leaves. Pipes 11 and 12 are aligned. Also shown are a supple sheath 15a in which is placed a bundle of optical fibers 15 and another supple sheath 13a which contains the optical fiber 13 of which only the end has been shown.

The optical fibers 13 and 15 are placed respectively inside a transparent case 16 and 17. Cases 16 and 17 are aligned and have a common axis x x1.

The pipe 11 terminates in a first blind bore 11a into which open two diametrically opposite bores or channels 18 and 19, of axis x x1. The two bores 18 and 19 cause the bore 11a to communicate with two chambers 20 and 21.

The transparent case 16 is in the form of a test tube or a glove finger, which is closed at one end by a rounded end 16a in the form of a spherical cap, which projects into the chamber 20, opposite bore 18. Similarly, transparent case 17 is in the form of a test tube closed at one end by an end 17a, in the form of a spherical cap, which projects into chamber 21 opposite bore 19.

The pipe 12 communicates with a blind bore 12a which communicates by bores 22 and 23 respectively with chambers 20 and 21.

The liquid to be monitored arriving via pipe 11 and 11a passes through the bores 18 and 19 and sweeps the spherical caps 16a and 17a, which has for its effect to avoid the risk of hydrocarbons or opaque particles adhering to these caps.

The liquid fills chambers 20 and 21. It emerges from the latter via bores 22 and 23 and it joins the outlet pipe 12.

The light beam which arrives via the optical fiber 13 passes through the transparent cap 17a, passes through the coaxial bores 18 and 19 then through the transparent cap 16a and it enters the optical fiber 15 which conducts it up to the photoelectric receiver located in the cabinet 14. The quantity of light transmitted from optical fiber 13 to optical fiber 15 depends on the opacity of the sheet of liquid located between the opposite ends of the two spherical caps 16a and 17a.

Referring again to FIG. 1, it is seen that the sample of liquid taken continuously through pipe 9 passes through a clarification unit 24 whose function is to separate from the liquid all the more or less opaque particles in suspension therein, other than hydrocarbons.

According to a feature of the invention, such separation is effected by means of a centrifuge rotating at a sufficiently high speed, for example a speed of the order of 7000 to 9000 rpm, for the particles in suspension, which are more dense than water, to be separated from the latter by centrifugal force. On the other hand, the hydrocarbons, which are lighter than water, tend to concentrate at the centre of the bowl of the centrifuge. There is therefore no risk of the hydrocarbons being separated and all the water and the hydrocarbons freed of the particles in suspension are found at the centrifuge outlet.

The bowl of the centrifuge 24 is driven in rotation by a motor 24a located in the rear compartment 4 and the drive shaft 24b which passes through the partition 2 comprises a stuffing box 24c.

Reference 25 represents a vane pump which is disposed between the outlet of the centrifuge 24 and the pipe 11 serving the measuring cell 10. Pump 25 mixes the water and the hydrocarbons emerging from the centrifuge and produces a very fine emulsion of the drops of hydrocarbons in the water, such condition being indispensable for correct operation of the optical measurement of the opacity due to the hydrocarbons.

The pump 25 is driven by a motor 25a placed in the rear compartment, via a shaft 25b which passes through partition 2 through a stuffing box 25c.

FIG. 1 shows that the optical measuring apparatus according to the invention complies with the inherent safety conditions since the front compartment 3 contains no motor nor any electrical or electronic circuit.

The vane pump 25 performs three functions. It produces a fine emulsion of water and hydrocarbons. It raises the pressure of the water taken by the pipe 9 to overcome the loss of pressure due to passage through the measuring cell 10, and to obtain at the outlet thereof a sufficient pressure to deliver the liquid up to the inlet of the decantation tank which is generally located on the ship's deck.

Figure 2:
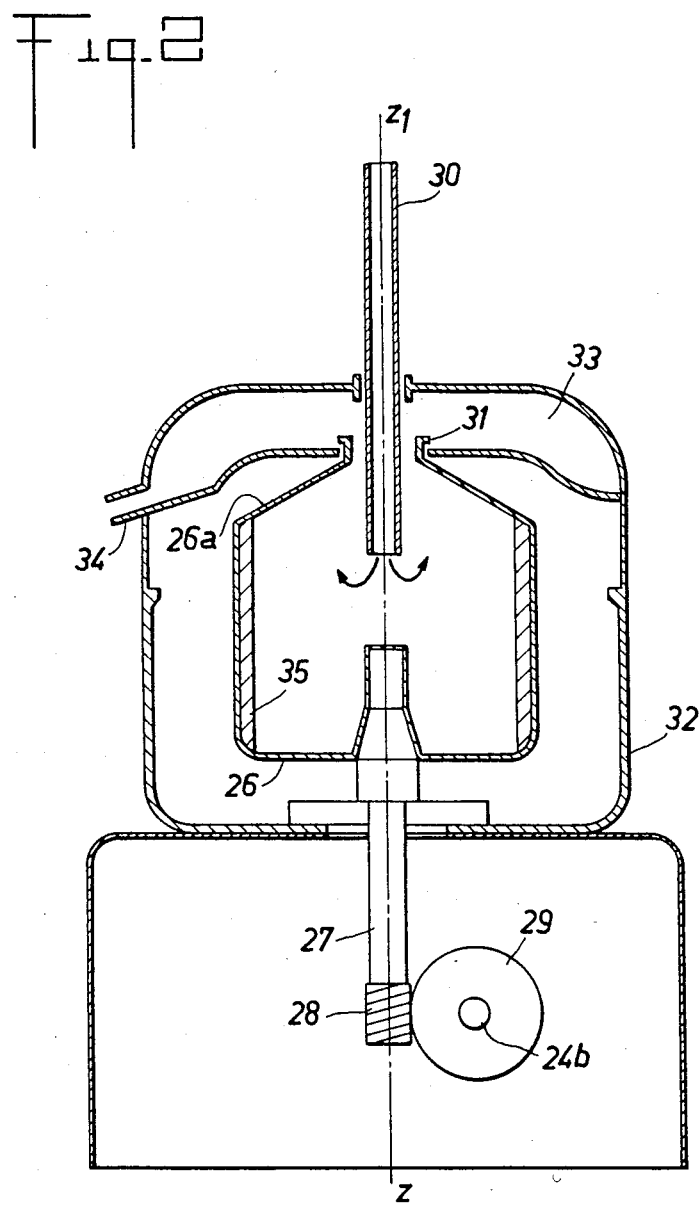
FIG. 2 is a vertical axial section through a centrifuge forming part of the apparatus according to the invention.

FIG. 2 shows a vertical section passing through axis z z1 of an embodiment of a centrifuge 24. It comprises a cylindro-conical bowl 26 of vertical axis z z1 which is mounted on a vertical drive shaft 27.

The shaft 27 is driven in rotation at a speed of the order of 7000 to 9000 rpm, for example by an endless screw 28 driven by a gear 29 which is mounted on the horizontal drive shaft 24b coming from motor 24a. Of course, the shaft 27 may be driven in rotation by any other equivalent mechanical transmission means.

The bowl 26 comprises at its upper end a truncated convergent portion 26a which defines an open neck 31 through which passes a fixed axial pipe 30 which opens out in the bowl.

The bowl 26 is placed inside a fixed casing 32 which surrounds the bowl and the drive shaft of the bowl in order to protect the operators in the event of mechanical rupture of the parts rotating at high speed. The neck 31 opens into a fixed chamber 33 which tops the casing 32. This chamber comprises one or more outlets 34 for evacuation of the liquid.

Operation is as follows: The liquid to be monitored, which is taken by pipe 9, arrives in the bowl via the pipe 30. It is driven in rotation at high speed. The particles in suspension in the liquid are entrained by the centrifugal force and are projected against the lateral walls of the bowl on which they are deposited, forming a layer 35.

The water and the hydrocarbons emerge from the centrifuge via neck 31 and flow towards the outlet 34. They are then sucked by the vane pump 25 which mixes the two non-miscible liquids energetically in order to form a very fine emulsion of hydrocarbons and water which is sent towards the optical measuring cell 10. The liquid which passes through cell 10 is freed of all the opaque particles which were in suspension in the liquid, such as sediments, silt or rust, and the measurement of opacity corresponds exactly to the hydrocarbon content.

The sediments accumulate against the walls of the bowl which can be easily dismantled for cleaning purposes. In a variant embodiment, a centrifuge may be used which incorporates automatic flushing, enabling the layer of sediments 35 to be periodically eliminated. In practice, the apparatus according to the invention, mounted on board an oil tanker, is used only during the first deballasting of the tanks which lasts about 20 hours and it is unnecessary to clean the bowl of the centrifuge during a crossing. It suffices to dismantle it and clean it upon arrival at the port or during the return trip during which there is no deballasting.

FIG. 2 shows a simplified centrifuge. Centrifuges which are usually used for clarifying liquids and for separating non-miscible liquids of different density, comprise a plurality of coaxial convergent portions which terminate in coaxial necks which each open out into a different chamber comprising an evacuation outlet.

If such a centrifuge were used, the coaxial convergent portion would collect the hydrocarbons lighter than water, whilst the peripheral convergent portion would collect the water. However, in the present application, there is no interest in separating the water and the hydrocarbons since they must then be mixed to form an emulsion.

A simplified centrifuge is therefore preferably used which comprises one convergent portion 26a and one chamber 33 which collects all the liquid emerging from the centrifuge.

Centrifuges exist, comprising bowls which are divided into a plurality of coaxial chambers by cylindrical baffles. Such centrifuges are used for treating liquids which are difficult to clarify or liquids not containing many particles in suspension.

FIG. 2 shows a centrifuge bowl comprising one chamber, but this choice is not limiting and centrifuges may be used whose bowl comprises a plurality of chambers defined by coaxial cylindrical partitions forming baffles, so that the liquid circulates from the centre towards the periphery and passes from one chamber to the following, passing around the partition which separates the two chambers.

Figure 3:
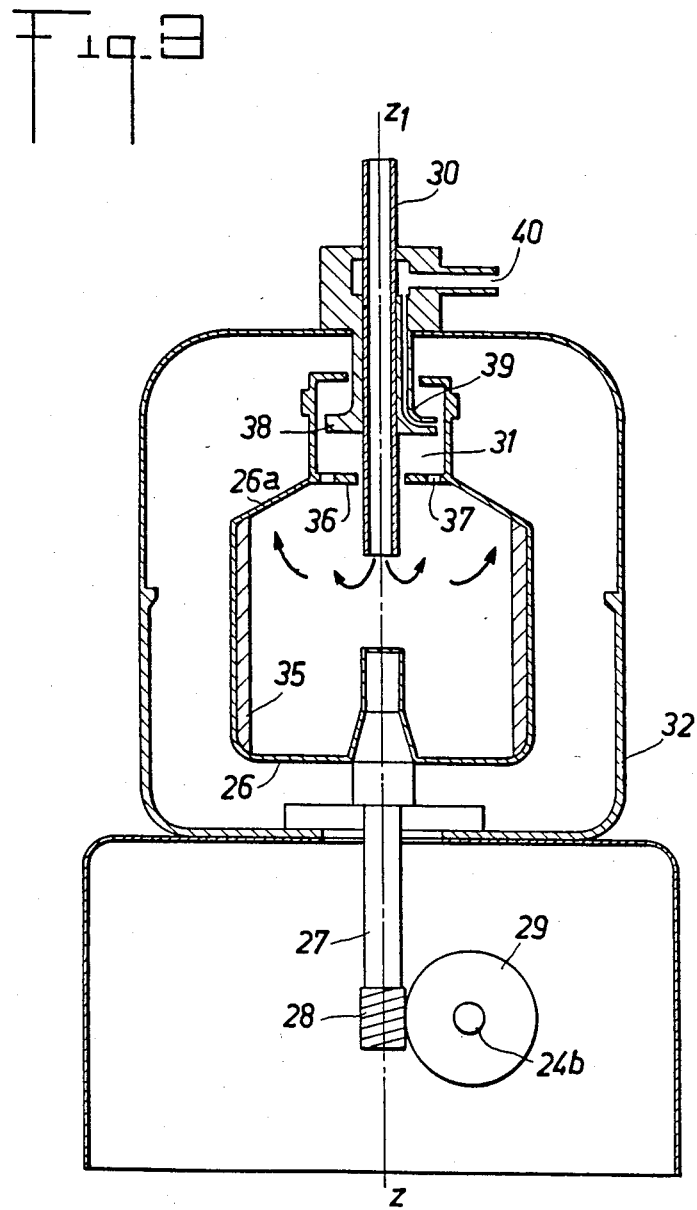
FIG. 3 is a vertical axial section through another embodiment of a centrifuge associated with an emulsifier.

FIG. 3 shows another embodiment of a centrifuge bowl used in an optical apparatus according to the invention.

Like parts are provided with like references in FIGS. 2 and 3. The only difference lies in the fact that the emulsifier pump 25 shown in FIG. 1 has been eliminated and is replaced by centripetal deflectors 38 which are incorporated in the centrifuge.

In this embodiment, the neck 31 communicates with the bowl 26 via a partition 36 comprising orifices 37. The partition 36 defines a chamber 31 through which the liquid which emerges from the centrifuge flows whilst being animated by a very rapid helicoidal movement. The chamber 31 is equipped with one or more centripetal turbines. The turbines are constituted by fixed deflectors 38 which are fast with the cover of the frame 32.

The deflectors 38 are disposed across the chamber 31. They comprise one or more centripetal pipes 39 having liquid inlet orifices located on the periphery of the deflectors. The pipes 39 open out into a pipe 40 through which the emulsion of water and hydrocarbons emerges.

The relative movement of the liquid with respect to the fixed deflectors 38 is the same as the relative movement with respect to a centripetal turbine rotor. The liquid which penetrates in the channels 39 is subjected to an intense, very turbulent mixing and the hydrocarbons are fractionated into very fine droplets which form an emulsion with the water.

Moreover, the speed of the liquid is transformed into pressure of the order of 4 bars, so that it is no longer necessary to interpose an emulsifier pump 25 between the centrifuge and the measuring cell 10, hence a saving in construction of the apparatus.

FIG. 3 shows an embodiment comprising one deflector 38 only, but a plurality of superposed deflectors may be used.

It will be readily understood that the apparatus according to the invention equipped with a centrifuge makes it possible continuously to eliminate the sediment, silt, rust and in general all solid or colloidal particles which are in suspension in the liquid and which would alter the optical measurement of the hydrocarbon content. Such elimination is made in a very short time, of the order of 8 to 10 seconds. It suffices that the bowl of the centrifuge have a sediment storage capacity of the order of 1 liter for the centrifuge to be able to contain all the sediments which must be separated in the course of one journey of the ship.

Taking into account the small quantity which flows through the measuring cell, it suffices to use a centrifuge whose bowl has a volume of some liters to clarify the liquid to be monitored before it passes into the measuring cell.

What is claimed is:

1. In an optical apparatus for continuously measuring the hydrocarbon content in a liquid, particularly deballast water in oil tankers containing particles in suspension, said apparatus being of the type comprising means for continuously sampling a quantity of said liquid, and an optical measuring cell equipped with a light source and a light receiver between which said quantity of said liquid circulates, the improvement which comprises a centrifuge disposed upstream of said measuring cell, which centrifuge comprises a bowl driven in rotation at high speed about a vertical axis and a truncated convergent portion topping said bowl, and a fixed chamber which collects all liquid emerging from said bowl, and includes at least one outlet, said truncated convergent portion defining an open neck which opens into said fixed chamber, and an emulsifier which mixes hydrocarbons and water contained in said liquid, and which is connected to said at least one outlet of said fixed chamber.

2. In an optical apparatus for continuously measuring the hydrocarbon content in a liquid, particularly deballast water in oil tankers containing particles in suspension, said apparatus being of the type comprising means for continuously sampling a quantity of said liquid and an optical measuring cell equipped with a light source and a light receiver between which said quantity of said liquid circulates, the improvement which comprises a centrifuge disposed upstream of said measuring cell, which centrifuge comprises a bowl driven in rotation at high speed about a vertical axis, a truncated convergent portion defining an open neck which tops said bowl, and fixed deflectors contained in said neck, and being placed across said neck to define therebetween centripetal conduits having inlet orifices located on the periphery of said deflectors so that rotating liquid flowing out of said bowl penetrates through said inlet orifices into said centripetal conduits to be finely emulsified therein.

3. The improved apparatus of claim 1, wherein said measuring cell comprises two diametrically opposite channels, two chambers each of which communicates with a respective one of said channels, a first blind bore into which said liquid flows and which is placed in communication with said two chambers by said channels, respectively, two transparent cases each of which terminates in a spherical cap located in a respective one of said two chambers opposite the opening of a respective one of said channels, and two optical fibers which are placed in said two transparent cases, respectively, and in alignment with said channels, and of which one connects said measuring cell to said light source and the other connects said measuring cell to said light receiver, said light receiver comprising a photoelectric receiver.

4. The improved apparatus of claim 3, further comprising a second blind bore which lies in alignment with said first blind bore, and conduits communicating said two chambers with said second blind bore.

* * * * *